United States Patent [19]

Yoo et al.

[11] 3,949,013

[45] Apr. 6, 1976

[54] COMPOSITION AND PROCESS

[75] Inventors: Jin Sun Yoo, Riverdale; Robert Koncos, Park Forest, both of Ill.

[73] Assignee: Atlantic Richfield Company, Philadelphia, Pa.

[22] Filed: Apr. 15, 1974

[21] Appl. No.: 460,862

Related U.S. Application Data

[63] Continuation of Ser. No. 187,116, Oct. 6, 1971, abandoned, which is a continuation of Ser. No. 753,052, Aug. 16, 1968, abandoned.

[52] U.S. Cl. ................... 260/683.15 D; 252/431 P
[51] Int. Cl.² ................................................ C07C 3/21
[58] Field of Search ........................... 260/683.15 D

[56] References Cited
UNITED STATES PATENTS

| | | | |
|---|---|---|---|
| 3,390,201 | 6/1968 | Drew | 260/683.15 D |
| 3,513,218 | 5/1970 | Faltings et al. | 260/683.15 D |
| 3,655,810 | 4/1972 | Chauvin et al. | 260/683.15 D |
| 3,709,953 | 1/1973 | Bergem et al. | 260/683.15 D |

*Primary Examiner*—Paul M. Coughlan, Jr.
*Attorney, Agent, or Firm*—Thomas J. Clough

[57] ABSTRACT

A solid phase catalyst for the polymerization, including oligomerization and codimerization, of olefins is provided by combining (A) a nickel source, (B) an electron donor ligand, and (C) a Lewis acid-reducing agent, in molar ratios of (B) to (A) of about 3 to 10:1 and (C) to (A) of about 2 or 3 to 40:1. Preferred catalyst components are nickel acetylacetonate, tri-n-butylphosphine, and ethylaluminum sesquichloride. Butenes and propylene are codimerized to provide yields of up to about 60% heptenes.

10 Claims, No Drawings

COMPOSITION AND PROCESS

This is a continuation, of now abandoned application Ser. No. 187,116, filed Oct. 6, 1971, which application is a continuation of application Ser. No. 753,052 filed Aug. 16, 1968, now abandoned.

This invention relates to a solid phase catalyst composition and its use in the polymerization, including codimerization and oligomerization, of olefins. In particular aspects, the invention relates to a process for the formation of heptenes by codimerization of propylene and butylene, and to a solid catalyst therefor.

Numerous catalysts have been disclosed in the prior art as suitable for the preparation of polymeric products of olefins, such as the low molecular weight dimers, trimers, tetramers, and the like. Other catalysts are known for the preparation of high molecular weight addition products, such as homopolymers and copolymers. These polymeric products derived from such reactions are often valuable materials in the petrochemical, fuel and plastics industries.

A proposed system having catalytic activity for the preparation of low molecular weight polymers is the homogeneous, liquid phase organo-phosphine complexes of transition metals such as nickel. Often included in such catalyst systems is a reducing agent, such as, for example, an alkyl aluminum halide, e.g. ethylaluminum sesquichloride, to create a more active catalyst. These complex catalysts are often prepared by contacting the transition metal, ordinarily as a salt, with an organophosphine at ambient or elevated temperatures to provide a complex in an inert solvent. To the complex in the solvent, the reducing agent is added to provide the more active species.

While the general scheme of the catalyst system has been described as being variable within considerable limits, no one, as yet, has disclosed a solid phase form of the catalyst. A solid phase catalyst is highly desirable for a number of reasons, including the ease of handling of solids as contrasted with liquids. In addition, a catalyst solid would be more readily and completely separated from the low molecular weight polymers commonly produced by such catalysts. When surface phenomena are considered a solid phase catalyst might also be more active and more selective than the homogeneous solution type of the same general ingredients. Despite these and other possible advantages, no solid phase catalyst of this type has been provided by the prior art.

A still further desirable characteristic for catalysts of such a system would be high specific activity for codimerization of different olefins. Olefins having different numbers of carbon atoms have different reactivities and it has not heretofore been possible to effectively codimerize different olefins utilizing the soluble catalyst systems of the foregoing type. Rather, when different olefins are contacted with the prior art catalysts, codimers are produced in only incidental amounts, while homo-dimers of each feed material predominates.

It is therefore an object of the present invention to provide a highly active catalyst for the polymerization, including codimerization and oligomerization, of low molecular weight olefins. It is a further object to provide such a catalyst in a solid phase. Another object of the present invention is to provide a catalyst for the polymerization of olefins having unusual stability. These and other objects apparent from the following disclosure are realized by the catalyst of the present invention.

It has been found that complexes of nickel with an electron donor ligand of organic-substituted elements of Group VA of the periodic table, said elements having an atomic weight of 15 to 83, when combined in controlled proportions with a non-protonic Lewis acid capable of forming a coordination bond with nickel, and a reducing agent capable of reducing nickel acetylacetonate to an oxidation state of less than 2, provide a solid phase composition having highly desirable physical and chemical characteristics and, particularly, excellent catalytic activity and selectivity for the polymerization, including codimerization and oligomerization, of low molecular weight olefins. The catalyst of the present invention has proved particularly effective in codimerizing olefins of differing reactivities, such as butene and propylene and the catalyst affords products containing relatively large quantities of normal and singlebranched chain structures. The solid catalysts of this invention are essentially black and either in amorphous or crystalline form, preferably amorphous, as determined by X-ray diffraction analysis. To obtain such solids the catalystforming reactants are combined in a molar ratio of electron donor ligand to nickel of about 3 to 10:1, preferably about 3 to 4:1; and a Lewis acid-reducing agent to nickel molar ratio of about 2 or 3 to 40 or more:1.

In the preparation of the catalyst composition of the present invention, the nickel source is provided by compounds of the metal which are at least slightly soluble in some solvent wherein the nickel-Group VA ligand complex can be formed. Preferred are the weak field complexes, the ligands of which readily serve in solution as transfer agents. Suitable sources of the nickel can include, for example, halides, e.g. $NiCl_2$, $NiBr_2$, $NiI_2$; dialkoxy nickel, i.e. $Ni(OR)_2$, where R represents alkyl, aryl, aralkyl, and the like groups; dialkoxy nickel carboxylate, i.e., $(RO)_2NiOOCR'$ where R and R' are as defined above as R; diphosphine complexes, e.g. $(Ni[(C_6H_5)_2PC_2H_4P(C_6H_5)_2]X_2$, where X is a halide. Also available as nickel sources are chelates formed by the nickel and weak field ligands, such as $\beta$-diketones or $\beta$-keto-carboxylic acid esters and salts of carboxylic acids. Examples of these types of nickel sources include $\beta$-diketonato nickel(II), acetylacetonato nickel(II), propylacetonato nickel(II), benzo-ylacetonato nickel; chelates from $\beta$-ketocarboxylic acids esters; salts of saturated monocarboxylic acids, e.g. nickel formate, nickel propionate, nickel caproate, nickel octoate, nickel palmitate, nickel stearate, nickel phenyl-acetate, nickel phenylpropionate, and the like; salts of corresponding unsaturated monocarboxylic acids, e.g. nickel acrylate, nickel vinyl acetate, and the like; salts of unsaturated dicarboxylic acids, e.g. nickel adipate, nickel decane-1,10-dicarboxylate, and the like; salts of corresponding unsaturated dicarboxylic acids, e.g., nickel muconate and the like; salts of cyclic and aromatic carboxylic acids, e.g., nickel cyclohexane carboxylate, nickel benzoate, nickel phthalates, and the like; and dialkoxy-carboxylates, e.g., nickel dimethoxyacetate and the like. Preferred as a source of nickel is nickel acetylacetonate.

The electron donor ligand component employed in preparing the nickel complex component of the catalyst of the present invention is preferably a triorganophosphine corresponding to the general formula $R_3P$ wherein R is a hydrocarbon radical, e.g. alkyl, aryl, alkaryl, aralkyl and cycloalkyl of from 1 to about 20 carbon atoms, preferably 2 to about 6 carbon atoms and devoid of olefinic or acetylenic unsaturation; different R groups may, of course, be present in the same phosphine molecule. When the phosphine component contains aromatic groups it is generally preferred that these have mono-cyclic structures, e.g., that the groups be selected from phenyl, alkylphenyl, or phenylalkyl radicals.

Multifunctional phosphines such as bis(diphenylphosphine) ethane may be used in place of the foregoing described unidentate phosphines. Phosphines may also be replaced by other electron donor ligands such as, for example, alkyl, aryl, alkaryl, aralkyl, or cycloalkyl phosphites, arsines, stilbines or bismuthines. Other monodentate or bidentate ligands containing nitrogen donating centers such as pyridine or alpha, alpha-bipyridyl, may also be utilized. It is, however, preferred that triorganophosphines be utilized. Examples of suitable phosphines for the composition of the present invention are triphenylphosphine, tri-methylphosphine, tricyclohexylphosphine, tri-n-hexylphosphine, tri-n-decylphosphine, tribenzylphosphine, tri-(4-n-butylphenyl) phosphine, and the like. Generally speaking, the electron donor ligand compounds of Group VA elements of the periodic table, having atomic numers of 15 to 83 can be used in our catalysts.

The Lewis acid and the reducing agent functions of our catalyst are preferably supplied in a single compound. As examples of such compounds, there may be mentioned the acidic metal halides which correspond to the general formula

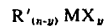

wherein M is a metallic element of coordination number n whose halides are Lewis acids, X is a halogen having an atomic number of 9 to 53, i.e. fluorine, chlorine, bromine, iodine. R' is hydrocarbyl, e.g., alkyl, of 2 to about 6 carbon atoms and y is a number having a value from greater than 0 to n. Preferred metallic elements in the above compound include aluminum, magnesium, beryllium, lead, zinc and tin. Examples of suitable such acidic metal halides include alkyl aluminum halides including mono-, sesqui-, and dihalides, aluminum trichloride, zinc chloride and stannic chloride. Specific examples of suitable alkylaluminum halides are diethylaluminum chloride, fluoride, iodide, and bromide; ethylaluminum dichloride; ethylaluminum sesquichloride, etc.

Where the particular reducing agent employed in the composition does not also perform as a Lewis acid, it is necessary to separately supply the Lewis acid to the catalyst composition. Examples of reducing agents which are suitable in the preparation of the catalyst composition but which do not perform as Lewis acids therein include trialkylaluminum, monoalkoxydialkyl- and dialkylaluminum hydrides wherein the alkyl and alkoxy groups contain up to about 6 carbon atoms. Other examples are Grignard reagents, allyl and alkyl tin complexes, and the like. The reducing agent must be compatible with the Lewis acid and be capable of reducing nickel acetylacetonate, preferably to an oxidation state lower than 1 and even to 0.

Where the reducing agent does not also function as a Lewis acid, an additional Lewis acid component can be supplied by a compound which is other than a protonic or hydrogen acid and which is capable of receiving one or more pairs of electrons to form a coordination bond. Lewis acids are well known to the art and are fully defined for example by Noller Chemistry of Organic Compounds, W. B. Saunders, 1951, at pages 233–235, by Stone Chemical Review (1958) at page 101, and by G. N. Lewis, Journal of the Franklin Institute (1938), pages 226–293. Examples of Lewis acids which are not included as a component of a compound which also serves as a reducing agent include boron-trifluoride, boron-trifluoride etherates, e.g. diethyletherate, aluminum trihalides, zinc halides and stannic halides.

The relative proportions of the components of the catalyst composition, i.e., the nickel, the Lewis acid and reducing agent, and the electron donor ligand, determine both the attainment of a solid phase and the catalytic character of the composition. In any event the molar ratios will be such that the catalyst composition is provided in the solid phase. However, it has been found that solid phase materials of differing activity and stability can be formed when the components are combined in various proportions. Among the solid phase materials isolated in the preparation of the composition of the present invention were three distinct species. One solid is an orange highly crystalline compound, formed with relatively low ratios of electron donor ligand and Lewis acid-reducing agent to nickel. X-ray diffraction analysis indicates a single crystal compound. The orange material, when treated with additional amounts of the Lewis acid-reducing agent component, is converted to a distinct, black, highly crystalline compound, having greater stability then the orange compound. X-ray diffraction analysis confirms that the black crystalline material is a different compound than the orange material. Further additions of the Lewis acidreducing agent component converted the black crystalline compound to a black, amorphous material, having the greatest activity and the greatest stability among the solid phase materials. Generally, it is the third, i.e. the black amorphous, form which is the preferred catalyst composition of the present invention, although the black and orange crystalline forms can be used as solid phase catalysts. However, lack of stability of the orange solid makes its use difficult.

The solid catalyst composition is ordinarily formed by using an electron donor ligand-to-nickel mole ratio of about 3 to 10:1, preferably about 3 to 4:1. The amount of the Lewis acid-reducing agent, e.g. ethyl aluminum sesquichloride, can preferably vary in more or less direct proportion with the ratio of electron donor ligand-to-nickel, generally increasing as the ligand is increased. The molar ratio of Lewis acid-reducing agent to nickel is preferably at least about the molar ratio of electron donor ligand to metal. Thus in producing the black amorphous catalyst form, the Lewis acid-reducing agent component can be used in a mole ratio to nickel, of at least about 3:1 when the ligand-to-nickel mole ratio is about 3:1, ranging up to at least about 10 or 12:1 when the ligand-to-nickel ratio is about 10:1. The Lewis acid-reducing agent need not ordinarily be utilized in a mole ratio of such agent to nickel of greater than about 40:1. In a preferred embodiment, the catalyst of the present invention comprises a black amorphous solid phase made from nickel acetylacetonate, tri-n-butylphosphine, and ethyl aluminum sesquichloride.

The catalyst of the present invention can be readily prepared by combining the three components in an inert solvent under a nitrogen atmosphere. For example, nickel acetylacetonate and tri-n-butylphosphine can be combined in appropriate amounts in, say, an autoclave or a glass container having a convenient amount of chlorobenzene, toluene or other solvent and stirred for about twenty minutes, or until a solid green precipitate forms. A solution of an appropriate amount of ethylaluminum sesquichloride in toluene or other solvent is added slowly. As the solution is continuously added, the green solid dissolves to form an orange-yellow catalytically active solution. Additional amounts of the ethylaluminum sesquichloride result in the formation, fleetingly, of the orange crystalline solid, then the black crystalline material, and finally the black amorphous compound. The black amorphous material is formed in a relatively fine colloidal dispersion, which because of its lyophilic nature can be difficult to separate from the solvent medium. However, digestion at elevated temperature and pressure, preferably with mild agitation, aids in coalescing the colloidal particles into larger, more readily separable form.

The colloidal precipitate separated from the liquid phase is an amorphous, tar-like material which is an active catalytic species for polymerizing low molecular weight olefins. The supernatent liquid shows little or no catalytic activity. Thus, the catalyst system can be operated in solid phase or as a slurry in which the finely divided precipitate is dispersed in an inert solvent for the olefin reactants. The solid catalyst can also be deposited on a support, such as activated carbon, etc. The catalytically-active solid is found to be soluble in polar solvents such as water, acetone, or alcohols, in which solvents the catalytic activity is destroyed. It is desirable to minimize, contact between the solid catalyst and moisture or air, since these are poisons of such catalysts as evidenced by a gradual color change from black to red and eventually to green. The present catalyst is much more stable toward these poisons than similarly constituted homogenous liquid phase catalyst reported in the prior art.

The catalyst of the present invention is useful either in slurry form in an organic solvent or as essentially dry particles disposed as a fixed bed, or in other convenient manner. The catalyst is able to overcome large differences in the reactivities of such olefins as butene and propylene molecules which tend to compete with one another in codimerization reactions. The present catalyst thus has excellent selectivity in codimerization of olefins. For example, the production of heptenes through the reaction of propylene and butene can be controlled readily by controlling several variables such as feed composition, feed rate, pressure, temperature and catalytic composition. Heptenes have been produced in amounts ranging from about 45 to 60%. The activity of the present catalyst is extraordinarily high so that the codimerization occurs under unusually mild conditions. Neither elevated temperature nor pressure is required for the codimerization of propylene and butene, although more rapid induction may make initial heating and pressurizing desirable. Once induction occurs, the exothermic nature of the reaction makes heating and/or pressurizing superfluous or even in some cases detrimental. Cooling of the system may be necessary in some instances.

The preparation of the overall catalyst composition is preferably conducted by first forming the complex of the electron donor ligand and the nickel source and then adding to a solution or suspension, of that complex, in a suitable organic solvent, the reducing agent and the Lewis acid. Suitable organic solvents for the final catalyst composition are those which are inert to the catalyst and which will not significantly enter into, or deleteriously affect, the eventual polymerization reaction. As specific examples thereof may be mentioned aromatic and aliphatic hydrocarbons and their halogenated, e.g. chlorinated, derivatives. Oxygen-containing solvents are generally to be avoided for this purpose.

Formation of the ligand-nickel complex may be effected by simply mixing the two reactants in the presence of a suitable solvent for the complexing reaction. The mixing may be done at room temperature or up to as high as about 300°F. The complex usually forms within about 20 to 40 minutes after mixing at elevated temperature. Suitable solvents for the complex-forming reaction include the same solvents which are suitable for use in the final catalyst composition. If desired, however, the complexing may be accomplished in a solvent which is unsuitable for use in the final composition; in this case the resultant complex will first be isolated from the reaction mixture and redissolved, or re-suspended, in a proper solvent which is inert to the final catalyst composition.

Thus, for example, one method of preparing a phosphine-nickel complex can involve stirring, preferably at room temperature, a mixture of tri-n-butylphosphine, nickel acetylacetonate and chlorobenzene. After the resulting solid, green complex has been formed there may then be added directly to the reactant mixture the reducing agent and Lewis acid.

In another method the complex may be prepared by refluxing an alcohol, e.g. ethanol, solution of the phosphine, say tri-n-butylphosphine, and nickel acetylacetonate, preferably at a temerature of about 150 to 250°F., and isolating the resultant complex from the reactant mixture. This approach is often preferred where the nickel reagent contains some water of hydration, as the water will be removed from the complex when the latter is separated from the alcohol solvent. The isolated complex can then be dissolved or suspended in a suitable inert solvent, e.g. chlorobenzene, and the reducing agent and Lewis acid added thereto to form the catalyst composition of the present invention.

The addition to the complex solution, of the reducing agent and Lewis acid is preferably conducted in a dry, inert atmosphere, out of the presence of air, for instance in an autoclave. Within a relatively short period of time after the admixing of the components, e.g. about 5 to 15 minutes, an active catalyst composition is formed as a colloidal precipitate which may be used to catalyze the polymerization of low molecular weight olefins.

The catalyst composition of the present invention may be used to catalyze the production of liquid polymers, including codimers and oligomers, of olefins of 2 to about 6, or even up to about 8, carbon atoms, as well as monophenyl-or diphenyl- derivatives thereof. Thus, suitable feeds include, for instance, mono-ethylenically unsaturated olefins, such as internal- and alpha-olefins, such as ethylene propylene and butenes; poly-ethylenically unsaturated olefins, preferably the dienes, such as butadiene-1,3, 1-alkyl-, 2-alkyl-, 2,3-dialkyl-1,3-butadienes; and phenyl-substituted derivatives of the foregoing olefins, such as styrene, 1,4-diphenylbutadiene-1,3 and 1-phenylbutadiene-1,3. The codimers or oligomers produced by the action of this present catalyst composition will often be of 2 to about 4 monomer units per molecule, i.e. will often range from dimers to tetramers. The catalyst composition has been found, for example, to be especially suitable for the production of heptene fractions by the codimerization of propylene and butene.

Polymerization can be effected by contacting the olefinically-unsaturated feed at an elevated temperature of, for instance, about 100° to 200°F., preferably about 120° to 170°F., which ordinarily can be maintained by the heat of reaction without external heating means. In many cases, it is necessary to control the temperature by cooling, as for example, by circulating a cooling medium through heat exchange tubes in the reactor. A pressure of about 10 to 500 psig, preferably about 200 to 500 psig, is suitable with the catalyst composition of the present invention. The amount of catalyst composition used in the reaction is that sufficient to effect polymerization of the feed, and often is about 0.05 to 5 weight percent, preferably about 0.1 to 1%, of catalyst composition (not including the solvent therefor) based on the weight of olefinic hydrocarbon feed. It has also been found that when the catalyst is prepared on a high surface area support, such as, for example, activated carbon, still other advantages, such as ease of handling, accrue.

The preparation and utilization of the catalyst of the present invention are illustrated by the following examples:

EXAMPLE I

In this example, the preparation of the catalyst is illustrated, utilizing a variety of proportions of the reactants. Two systems are investigated, utilizing in one instance nickel acetylacetonate, ethyl aluminum sesquichloride, and tri-n-butyl phosphine, and in the second, nickel acetylacetonate, ethyl aluminium sesquichloride, and triphenyl phosphine.

The procedures utilized in the various runs of the present example were as follows: The indicated amounts of the nickel acetylacetonate and the phosphine were dissolved in 40 milliliters of toluene in a 150 ml. Erlenmeyer flask. After a purge with nitrogen, a solution of ethyl aluminum sesquichloride in toluene was added from a microburet via a syringe needle. During the entire period, no heating was applied and air was excluded. Details of the operation and results appear in Table I.

TABLE I

| Run No. | $Ni(acac)_2^{(1)}$ m. moles | $R_3P^{(2)}$ m. moles | $Et_3Al_2Cl_3^{(3)}$ m. moles | Observation |
|---|---|---|---|---|
| 1 | 0.99 | 3.00 | 1.65 | Red solution |
|   |      |      | 2.31 | Red solution |
|   |      |      | 2.64 | Black solution |
|   |      |      | 3.30 | Black, viscous system. Black, amorphous precipitate forms overnight |
| 2 | 1.01 | 4.00 | 2.64 | Red solution, becomes dark brown with trace of black ppt. after 2 days |
| 3 | 1.01 | 5.00 | 3.96 | Dark red soln., minor amt. ppt. |
|   |      |      | 5.61 | Black, viscous liquid with black tar-like ppt. |
| 4 | 1.01 | 6.00 | 3.30 | Red soln. |
|   |      |      | 3.96 | Dark red soln. |
|   |      |      | 4.95 | Light orange soln. |
|   |      |      | 7.92 | Black, dense system; in two days, ppt. forms. |
|   |      |      | ↓    |  |
|   |      |      | 11.55 | ditto |
| 5 | 1.01 | 7.00 | 4.62 | Dark red soln. |
|   |      |      | 6.27 | Black, viscous system, black, oily sediment |
| 6 | 1.00 | 10.00 | 5.94 | Red soln. |
|   |      |       | 7.59 | Dark red soln. |
|   |      |       | 10.56 | Black system, no. ppt. |
|   |      |       | 12.05 | Black, viscous system. |
| 7 | 0.99 | 3.03 | 0.33 | Orange red soln. unreacted $Ni(acac)_2$ |
|   |      |      | 1.98 | Light orange liquid with some black solid and a large amount of orange crystals |
| 8 | 1.00 | 3.00 | 0.16 | Dark red soln. |
|   |      |      | 0.66 | ditto |
|   |      |      | 1.32 | Darker red soln. turns to light orange |
|   |      |      | 2.65 | Dark orange soln. |
|   |      |      | 3.96 | Black, viscous system with large amount of black tar-like material |
|   |      |      | ↓    |  |
|   |      |      | 4.29 |  |
| 9 | 0.99 | 5.79 | 1.98 | Black crystalline |

TABLE I-continued

| Run No. | Ni(acac)$_2$[1] m. moles | R$_3$P[2] m. moles | Et$_3$Al$_2$Cl$_3$[3] m. moles | Observation |
|---|---|---|---|---|
| 10 | 1.00 | 9.77 | 3.30 | ppt. Clear orange soln. |
|  |  |  | 8.25 | Light orange soln. |
|  |  |  | 11.55 | Dark orange soln. |
|  |  |  | 14.85 | Black, viscous system with black amorphous precipitate |
| 11 | 1.02 | 3.14 | 3.90 | Black crystals and orange needle-shaped crystals in orange solution |
| 12 | 0.96[4] | 3.0 | 0.83 | Yellow soln. with unreacted NiCl$_2$ |
|  |  |  | 2.48 | Clear light brown soln. w/unreacted NiCl$_2$. In 2 days an orange, clear soln. with small amount of black solid material |
| 13 | 1.07[4] | 6.0 | 3.47 | Red to yellow soln. w/some unreacted NiCl$_2$ |
|  |  |  | 4.29 | Brown soln. w/unreacted NiCl$_2$, turned black-brown. Black viscous system in 2 days. |

[1] Ni(acac)$_2$ is nickel acetylacetonate.
[2] R$_3$P is tri-n-butylphosphine in runs 1 to 6, 12 and 13 and triphenylphosphine in runs 7–11.
[3] Et$_3$Al$_2$Cl$_3$ is ethylaluminum sesquichloride.
[4] NiCl$_2$ used rather than Ni(acac)$_2$.

It is apparent from Table I that the form of the catalyst can be varied by varying the proportions of the various reactants. The catalytic activity of various solid phase catalyst compositions of the present invention as investigated, and appear as Examples II to XI below. Percentages herein are by weight unless indicated otherwise.

EXAMPLE II

A 300 cc. stainless steel autoclave, equipped with an air driven magnetic stirrer, was charged with 2.9 millimoles of nickel acetylacetonate with 30 grams of chlorobenzene. After the reaction vesseel was purged with nitrogen for 30 minutes, 12.2 millimoles of tri-n-butylphosphine was injected to the system through a serum cap. These materials were vigorously stirred at room temperature under a nitrogen atmosphere for about 20 minutes to form a distinctive green complex. Ethylaluminum sesquichloride in a toluene solution was injected slowly through the serum cap by means of a syringe and needle until 25 millimoles of ethylaluminun sesquichloride were added. The total amount of toleuene added, including a wash of the syringe after the addition, was 20 grams. The system was then stirred vigorously for fifteen minutes to form the catalytically-active species as a slurry in the mixed solvents.

A mixed liquid feed of approximately 25% butene-1 and 75% propylene, designated Type B, was slowly fed into the system without heating. Soon after the feed was introduced, the temperature of the system rapidly increased due to the exothermicity of the reaction. Water cooling was provided to maintain the temperature at 100° to 140°F. throughout the reaction. A total of two hundred ten milliliters of the feed were added at a rate of about 2 ml. per minute. A pressure drop occurred over the entire period of addition, to provide a pressure in the final stages of the addition of about 60 psig. After the feed addition was discontinued, the reactor was maintained at temperature for about 30 minutes, during which time the pressure dropped from 60 to 55 psig. The straw colored reaction mixture was discharged from the reactor with a minor amount of the black catalyst solids. The major amount of the catalyst remained as a deposit on the walls of the reaction vessel. The reaction mixture was treated with dilute aqueous hydrochloric acid, and an organic layer was separated from the lower aqueous portion. The organic portion was distilled and the products were identified by gas-liquid phase chromatography, and gas-liquid phase chromatography with prior hydrogenation. A large portion, about 60%, of heptene products were obtained along with about 10% hexenes and about 20% octenes which show the homopolymerization activity of the catalyst. Details of the reaction conditions, the catalyst composition and reaction products are in Table II.

EXAMPLE III

By the procedure outlined in Example II, a second catalytic composition was prepared utlizing 2.7 millimoles of nickel acetylacetonate, 11.6 millimoles of tri-n-butylphosphine, and 27.1 millimoles of ethylaluminum sesquichloride in 64 grams of solvent, all of which was chlorobenzene rather than the mixed solvent used in Example II. The catalyst formed as a black colloidal precipitate dispersed in the solvent medium and was stirred for about ten minutes at room temperature.

About 230 milliliters of mixed butene-1 and propylene, Type B feed, were continuously added to the reactor from a blowcase over a period of about 95 minutes. After a brief induction period, the temperature was maintained at 120° to 150°F. with water cooling. The pressure during addition was about 37 to 76 psig until the last few milliliters of the feed were introduced, which raised the pressure of the system to 300 psig. A rapid pressure drop ensued, and in about ten minutes, the pressure had decreased to 147 psig, indicating that higher pressures are favorable to the reaction. The reaction mixture was discharged and processed as in Example II, producing about 50% heptenes and a conversion, based on propylene fed, of about 90%. Details of the reaction and products appear in Table II.

EXAMPLE IV

A catalyst was prepared as in Example II utilizing 2.7 millimoles of nickel acetylacetonate, 12.2 millimoles of tri-n-butylphosphine, and 25.0 millimoles of ethylaluminum sesquichloride in a solvent mixture of 25 grams chlorobenzene and 20 grams toluene. About 220 milliliters of a feed of approximately 70% butene-2, 30% propylene, designated Type C feed, was continuously introduced at 0 to 30 psig over a period of 120 minutes. The temperature was maintained at 81° to 145°F. The reaction was stopped as soon as the feed was completely introduced by discharging the reaction mixture and deactivating the catalyst with dilute aqueous hydrochloric acid. The product was analyzed as in Example II and found to contain about 50% heptenes with about 18% hexenes and 32% octenes. Further details of the work appear in Table II.

and propylene was continuously fed into the catalyst slurry for 20 minutes at 100° to 120°F. and 40 to 70 psig until about 220 milliliters were added. The system was allowed to react for an additional 15 minutes after completion of the feed addition. During this period, the pressure dropped from 70 to 50 psig and the temperature dropped from 120° to 100°F. The orange colored reaction mixture was discharged, leaving most of the catalyst solids deposited on the inside surfaces of the reactor. The mixture was treated as in previous examples, while the catalyst was preserved for additional runs.

A second run was started immediately after the withdrawal of the liquid reaction mixture from the first run was complete. The same mixed feed was introduced into the reactor with the solid catalyst over a period of ten minutes at 100° to 120°F. and 60 to 140 psig until 290 milliliters had been added. The reaction was continued for an additional five minute period during which the temperature dropped from 120° to 105°F., and the pressure dropped from 140 to 100 psig. The yellow reaction mixture was withdrawn and a third and fourth additional runs were conducted in the same manner as the second. After the fourth run, the solid catalyst in the reactor was maintained under a nitrogen atmosphere for ten hours. A fifth run was then conducted on the aged catalyst under the same conditions as the preceding runs. The reaction mixtures in each run were treated, as in previous examples, by deactivating the catalyst with dilute aqueous hydrochloric acid, separating the organic layer from the aqueous material, distilling to insure separation from any soluble catalyst residue, and then analyzed. Further details of the work appear in Table III. It should be noted that the activity of the catalyst is maintained for substantial periods.

TABLE II

The Catalytic Cross-dimerization of Butenes and Propylene
A. Product Distribution

| Example No. | Type of Feed | Product Distribution Weight % | | | | Heavy Product g. | Total Product Obtained g. | Conversion (%) Based on $C_3$=Fed | Total Conversion |
|---|---|---|---|---|---|---|---|---|---|
| | | $C_6=$ | $C_7=$ | $C_8=$ | $C_9=$ | | | | |
| II | B | 11.8 | 59.6 | 28.7 | — | 6.0 | 64 | 63.4 | 49.5 |
| III | B | 10.6 | 47.9 | 41.4 | — | — | 97 | 88.4 | 70.3 |
| IV | C | 17.7 | 50.8 | 31.5 | — | — | 68 | 78.4 | 57.8 |

TABLE II

B. The Catalytic Components and Reaction Conditions

| Example No. | Catalytic Components | | | Solvent g | Form of Catalyst | Reaction Conditions | | |
|---|---|---|---|---|---|---|---|---|
| | $Ni(acac)_2$ m. moles | $(n\text{-}Bu)_3P$ m. moles | $Et_3Al_2Cl_3$ m. moles | | | Press. psig | Temperature °F. | Reaction Time, Min. |
| II | 2.9 | 12.2 | 25.0 | 50 | slurry | 17–60 | 100–140 | 105 |
| III | 2.7 | 11.6 | 27.1 | 64 | slurry | 37–70 | 120–147 | 95 |
| IV | 2.7 | 12.2 | 25.0 | 45 | slurry | 2–30 | 80–145 | 120 |

EXAMPLE V

A catalyst slurry was prepared in the autoclave reactor in the manner of Example II with 2.3 millimoles of nickel acetylacetonate, 11.5 millimoles of tri-n-butylphosphine, and 16.0 millimoles of ethylaluminum esquichloride, in 33 grams of chlorobenzene and 11 grams of toluene. The type B mixed feed of butene-1

The observed trend of decreasing activity is somewhat offset by the fact that small, but appreciable, amounts of the catalyst were removed at the end of each run with the reaction mixtures, and partly because no particular efforts were taken to exclude from the catalysts such poisons deactivators such as water and air. Despite the rapid introduction and short reaction times, substantial fractions of heptenes were obtained.

TABLE III

The Catalytic Cross-Dimerization of Butene-1 and Propylene
A. Product Distribution (Wt. %)

| Example No. | Run No. | Type of Feed | $C_6=$ | $C_7=$ | $C_8=$ | $C_9=$ | Heavy Product | Total Product g. | Conversion (%) Based on $C_3=$Feed | Total Conversion |
|---|---|---|---|---|---|---|---|---|---|---|
| V | 1st | B | 17.1 | 48.1 | 34.8 | — | — | 68 | 67.8 | 45.0 |
|   | 2nd | B | 39.0 | 43.2 | 17.8 | — | — | 48 | 65.6 | 28.2 |
|   | 3rd | B | 60.4 | 31.7 | 6.25 | 1.68 | — | 20 | 51.1 | 16.9 |
|   | 4th | B | 57.8 | 31.9 | 10.29 | — | — | 21 | 37.4 | 13.0 |
|   | 5th | B | 45.7 | 36.6 | 17.8 | — | — | 11 | 16.3 | 6.2 |

TABLE III

B. Catalyst Components and Reaction Conditions

| Example No. | Run No. | Catalytic Components Ni(acac)$_2$ m moles | (n-Bu)$_3$P m moles | Et$_3$Al$_2$Cl$_3$ m moles | Solvent g. | Catalytic Form. | Press. Psig | Reaction Conditions Temperature °F. | Reaction Time Min. |
|---|---|---|---|---|---|---|---|---|---|
| V | 1st | 2.3 | 11.5 | 16.0 | 44 | Slurry | 40–70 | 100–120 | 35 |
|   | 2nd | —————Solid Catalyst————— | | | 0 | Solid | 60–140 | 105–120 | 15 |
|   | 3rd | Solid Catalyst | | | 0 | Solid | 65–100 | 95–05 | 20 |
|   | 4th | Solid Catalyst | | | 0 | Solid | 80–120 | 95–98 | 17 |
|   | 5th* | Solid Catalyst | | | 0 | Solid | 55–600 | 75–80 | 95 |

*The solid catalysts in the reactor were left under nitrogen overnight (10 hours) before 5th run began.

EXAMPLE VI

A catalyst slurry was prepared by combining 2.9 millimoles nickel acetylacetonate, 12.2 millimoles tri-n-butyl phosphine, and 36.0 millimoles of ethylaluminum sesquichloride in 30 grams of chlorobenzene and 26 grams of toluene by the procedure of Example II. About 230 milliliters of feed Type B were added in the course of 110 minutes at 85° to 155°F. and 0 to 70 psig. After a holding time of ten additional minutes, the reaction mixture was discharged.

The solid catalyst left from the first run was used for a second run. 208 milliliters of the same feed were continuously added over 75 minutes at 115° to 165°F. and 60 to 150 psig. Data regarding both reactions and reaction mixtures appear in Table IV.

EXAMPLE VII

The procedure of Example VI was repeated with a catalyst prepared from 3.2 millimoles of nickel acetylacetonate, 12.2 millimoles of tri-n-butylphosphine, and 35 millimoles of ethylaluminum sesquichloride, in 35 grams of chlorobenzene and 27 grams of toluene. Details of the work appear in Table IV.

TABLE IV

Catalytic Cross-dimerization of Butene and Propylene
A. Product Distribution (Wt. %)

| Example No. | Run No. | Type of Feed | $C_6=$ | $C_7=$ | $Ch_8=$ | $C_9=$ | Heavy Product | Total Product g. | Conversion (%) Based on $C_3=$Feed | Total Conversion |
|---|---|---|---|---|---|---|---|---|---|---|
| VI | 1st | B | 10.3 | 45.7 | 44.1 | — | — | 77 | 87.8 | 55.5 |
|    | 2nd | B | 25.5 | 48.5 | 33.7 | 5.5 | — | 113 | ~100 | 51.8 |
| VII | 1st | B | 15.9 | 46.6 | 37.5 | — | — | 67 | 67.4 | 46.8 |
|     | 2nd | B | 48.3 | 44.0 | 6.4 | 1.2 | — | 58 | 93.8 | 33.7 |

TABLE IV

B. Catalytic Components and Reaction Conditions

| Example No. | Run No. | Catalytic Components Ni(acac)$_2$ m moles | (n-Bu)$_3$P m moles | Et$_3$Al$_2$Cl$_3$ m moles | Solvent g. | Catalytic Form. | Press. Psig | Reaction Condition Temperature °F. | Reaction Time Min. |
|---|---|---|---|---|---|---|---|---|---|
| VI | 1st | 2.9 | 12.2 | 36 | 56 | Slurry | 0–70 | 155–165 | 120 |
|    | 2nd | ——————Solid catalyst—————— | | | 0 | Solid | 60–160 | 115–165 | 75 |
| VII | 1st | 3.2 | 12.2 | 35 | 62 | Slurry | 20–140 | 105–128 | 46 |
|     | 2nd | ——————Solid catalyst—————— | | | 0 | Solid | 100–180 | 335 | 45 |

EXAMPLE VIII

A solid catalyst slurry was prepared by the technique of Example II from 2.3 millimoles of nickel acetylacetonate, 10.7 millimoles of tri-n-butylphosphine, and 22.2 millimoles of ethylaluminum sesquichloride in 27.5 grams of chlorobenzene and 16.5 grams of toluene. A feed designated Type A having about 58% propylene and 42% butene-1 was utilized. Over a period of thirty minutes, 280 milliliters of the feed were added to the catalyst slurry at 90° to 115°F, and 20 to 50 psig. The reaction was continued for ten more minutes and the reaction mixture was discharged with a minor amount of catalyst solids. The remainder of the catalyst was retained in the reactor and utilized in subsequent runs 2–4.

The subsequent runs were conducted by passing 280 milliliters of Type A or B feeds to the catalyst under the conditions specified in Table V. Examination of the analyses in Table V indicate that the heptene fraction in these runs is lower than when the Type B feed, predominating in butenes, is utilized. Thus the ratio of butene to propylene appears to be a significant factor in determining the selectivity to heptenes. The molar ratio of butene to propylene in the feed should be greater than 1 if the better heptene selectively is to be maintained. In such a fashion, the butene molecules are apparently more readily activated by virtue of more direct contact with the catalytic nickel sites. It is possible to approximate the ideal of adding fresh propylene to catalytically activated butene by controlling the reaction conditions, feed ratio, feed rate, and the composition of the catalyst chloride in 41 grams of mixed solvent, by the technique of Example II. The catalyst was contacted with a feed comprised of approximately 56% isobutene and 44% propylene, designated Type D feed, by adding 230 milliliters over a period of 25 minutes at 80° to 116°F. and 60 to 150 psig. After stirring for one hour, the reaction mixture was withdrawn and treated as in previous examples. The analyses appearing in Table VI indicates that heptene and even octene yields were considerably lower than in runs with butene-1 and butene-2. The reactivity of isobutene could be enhanced by more favorable reaction conditions; however, it seems that isobutene tends to favor homooligomerization rather than codimerization with propylene under the reaction conditions employed.

TABLE V

Catalytic Cross-dimerization of Butenes and Propylene
A. Product Distribution

| Example No. | Run No. | Type of Feed | Product Distribution (Wt. %) | | | | Heavy Product | Total Product g. | Conversion (%) | |
|---|---|---|---|---|---|---|---|---|---|---|
| | | | $C_6=$ | $C_7=$ | $C_8=$ | $C_9=$ | | | Based on $C_3=$Feed | Total Conversion |
| VIII | 1st | A | 52.8% | 30.4 | 11.3 | | 5.5 | 103 | 82.2% | 72.3% |
| | 2nd | A | 66.8 | 29.6 | 2.0 | 1.5 | — | 89 | 74.9 | 72.0 |
| | 3rd | A | 79.4 | 16.1 | 1.2 | 3.8 | 0.5 | 93 | 97.2 | 63.2 |
| | 4th | B | 54.7 | 36.7 | 8.6 | — | — | 44 | 74.5 | 26.1 |

TABLE V

B. Catalyst Components and Reaction Conditions

| Example No. | Run No. | Catalytic Components | | | Solvent g. | Catalytic Form. | Press Psig | Reaction Condition Temperature °F. | Reaction Time Min. |
|---|---|---|---|---|---|---|---|---|---|
| | | $Ni(acac)_2$ m moles | $(n-Bu)_3P$ m moles | $Et_3Al_2Cl_3$ m moles | | | | | |
| VIII | 1st | 2.3 | 10.7 | 22.2 | 44 | Slurry | 20–50 | 90–115 | 45 |
| | 2nd | ————Solid Precipitate———— | | | 0 | Solid | 170–400 | 100 | 48 |
| | 3rd | Solid Precipitate | | | 0 | Solid | 60–160 | 125 | 55 |
| | 4th | Solid Precipitate | | | 0 | Solid | 125–210 | 135 | 90 |

EXAMPLE IX

A catalyst slurry was prepared by the technique of Example II from 4.3 millimoles of nickel acetylacetonate, 33.6 millimoles of tri-n-butylphosphine, and 60 millimoles of ethylaluminum sesquichloride, in 80 grams of mixed chlorobenzene and toluene solvents. A mixed butene-1 and propylene feed of Type B was bubbled through the slurry at atmosphereic pressure without supplying heat. The effluent gases from the reactor were connected to both a condenser and a cold trap. About five minutes after the feed was started, the temperature increased to 60° to 65°C. from the heat liberated in the reaction. The feed was continued for about 1 ½ hours to provide about 7–8 grams of product. The feed was then discontinued and the catalyst was aged for about 16 hours. The same reaction was then again started under the same conditions and continued for another two hours. About 15 grams of additional product were recovered. The catalyst was still active when the reaction was discontinued. The colloidal catalyst particles were slowly coalesced to a larger particle size during the reaction. The results of the operation appear in Table VI.

EXAMPLE X

A catalyst slurry was prepared from 2.3 millimoles of nickel acetylacetonate, 9.2 millimoles of tri-n-butylphosphine, and 18 millimoles of ethylaluminum sesqui-

EXAMPLE XI

About 9.0 grams of activated carbon were added to a saturated methanol solution of 3.0 millimoles of nickel acetylacetonate and the solution was allowed to impregnate the carbon black for several hours. The methanol was then allowed to evaporate and the impregnated carbon was dried at 100°C. for 30 minutes. A solution of 17.3 millimoles of tri-n-butylphosphine in chlorobenzene was injected onto the nickel-impregnated carbon under nitrogen, and after twenty minutes, a solution of 24 millimoles of ethylaluminum sesquichloride in 20 milliliters of toluene was added. The resulting dark mixture was allowed to stand for several hours. When the liquid phase became much less dark, the liquid was separated from the solids, which were then washed with toluene until the wash effluent was clear.

The catalyst supported on carbon was transferred to the reactor, with no attempt to exclude air. The reactor was then purged with nitrogen for twenty minutes. Over a period of 130 minutes, 250 millilters of mixed butene-1 and propylene, feed Type B, were continuously fed at 130° to 150°F. and 90 to 110 psig. The reaction mixture was discharged, treated and analyzed as in previous examples. Further details of the work appear in Table VI.

TABLE VI

Catalytic Cross-dimerization of Butenes and Propylene
A. Product Distribution

| Example No. | Type of Feed | Product Distribution (Wt. %) | | | | | Total Product g. | Conversion (%) | |
|---|---|---|---|---|---|---|---|---|---|
| | | $C_6=$ | $C_7=$ | $C_8=$ | $C_9=$ | Heavy Product | | Based on $C_3$ Feed | Total Conversion |
| IX | B | 83.4 | 14.8 | 0.4 | — | 1.41 | 21 | — | — |
| X | D | 93.2 | 4.7 | 2.6 | — | — | 103 | 98 | 72 |
| XI | B | 21.1 | 48.5 | 30.7 | — | — | 49.0 | 55.6 | 32.7 |

TABLE VI

B. Catalyst Components and Reaction Conditions

| Example No. | Catalytic Components | | | Solvent g. | Catalytic Form. | Press. Psig | Reaction Conditions | |
|---|---|---|---|---|---|---|---|---|
| | $Ni(acac)_2$ m. moles | $(n-Bu)_3P$ m. moles | $Et_3Al_2Cl_3$ m. moles | | | | Temperature °F. | Reaction Time Min. |
| IX | 4.3 | 33.6 | 60.0 | 80 | Slurry | 0 | 105–125 | 105 |
| X | 2.3 | 9.2 | 18.2 | 41 | Slurry | 60–140 | 80–125 | 85 |
| XI | 3.9 | 17.3 | 24.0 | 0 | Supported on Carbon | 90–110 | 130–150 | 130 |

We claim:

1. In a process for polymerizing monoethylenically unsaturated olefins of 2 to about 8 carbon atoms to dimers through tetramers, the improvement which comprises polymerizing said olefin in contact with a solid catalyst which comprises a black amorphous (as determined by X-ray diffraction), solid reaction product of a complex of
   A. a nickel compound at last slightly soluble in a solvent wherein the complex of (A) and (B) is formed, and
   B. a hydrocarbon phosphine electron donor ligand, with
   c. a combination of reducing agent capable of reducing nickel acetylacetonate to an oxidation state of less than 2, and non-protonic Lewis acid capable of forming a coordination bond with nickel; said reactants being combined in a molar ratio of (B) to (A) of about 3 to 10:1 and a molar ratio of (C) to (A) of about 2 to 40:1, said components (C) and (A) being combined to reduce nickel represented by (A) to an oxidation state of less tha 2, and said components (C), (B) and (A) being combined to produce a black amorphous catalyst and an effective polymerization catalyst and the polymerization is conducted in the substantial absence of any organic solvent used in the preparation of the catalyst.

2. The process of claim 1 wherein the olefin polymerized consists essentially of a plurality of monoolefins differing in their number of carbon atoms.

3. The process of claim 2 wherein the olefin polymerized is a mixture of propylene and normal butene.

4. The method of claim 1 wherein (C) is an aluminum alkyl halide.

5. The process of claim 4 wherein the hydrocarbon phosphine is of the formula $R_3P$ wherein R is hydrocarbon of 1 to about 20 carbon atoms and is devoid of olefinic and acetylenic unsaturation.

6. The process of claim 4 wherein component (C) is an aluminum alkyl sesquichloride.

7. The process of claim 6 wherein the olefin polymerized consists essentially of a plurality of monoolefins differing in their number of carbon atoms.

8. The process of claim 7 wherein the olefin polymerized is a mixture of propylene and normal butene.

9. The process of claim 4 wherein component (C) is an aluminum alkyl sesquichloride and (B) is a hydrocarbon phosphine whose hydrocarbon groups have 2 to about 6 carbon atoms.

10. The process of claim 9 wherein nickel of component (A) is supplied by nickel acetylacetonate.

* * * * *